United States Patent
Feldsine et al.

(10) Patent No.: US 6,379,918 B1
(45) Date of Patent: Apr. 30, 2002

(54) COMPOSITION, FORMULAE, DEVICES AND METHODS FOR CONTROL OF SPECIFICITY AND INCLUSIVITY OF MICROORGANISMS CONTAINING CLOSELY RELATED ANTIGEN EPITOPES

(75) Inventors: Philip T. Feldsine, Mercer Island; David E. Kerr, Seattle; Ping Zhu; Linda Mui, both of Kirkland, all of WA (US)

(73) Assignee: Biocontrol Systems, Inc., Bellevue, WA (US)

( * ) Notice: Subject to any disclaimer, the term of this patent is extended or adjusted under 35 U.S.C. 154(b) by 0 days.

(21) Appl. No.: 09/374,560

(22) Filed: Aug. 13, 1999

Related U.S. Application Data
(60) Provisional application No. 60/096,566, filed on Aug. 14, 1998.

(51) Int. Cl.$^7$ .................................................. C12Q 1/04
(52) U.S. Cl. .................. 435/34; 435/7.1; 435/7.32; 435/7.35; 435/7.72; 435/7.94; 435/7.95; 435/30; 435/38; 435/39; 435/173.4; 435/244; 436/501; 436/536; 436/539; 530/388.1; 530/389.1
(58) Field of Search ............................ 435/7.32, 7.35, 435/7.72, 7.94, 7.95, 30, 34, 38, 39, 173.4, 173.8, 173.9, 244, 287.2, 7.1; 436/501, 514, 536, 539; 530/388.1, 389.1

(56) References Cited

U.S. PATENT DOCUMENTS

| | | | | |
|---|---|---|---|---|
| 5,415,997 A | * | 5/1995 | Atrache et al. | 435/7.35 |
| 5,726,062 A | | 3/1998 | Numa et al. | 436/86 |
| 5,807,694 A | | 9/1998 | Zawistowki | 435/7.35 |

FOREIGN PATENT DOCUMENTS

| | | |
|---|---|---|
| WO | WO 92/02820 | 2/1992 |
| WO | WO 95/30903 | 11/1995 |
| WO | WO 98/22824 | 5/1998 |
| WO | WO 98/27432 | 6/1998 |

OTHER PUBLICATIONS

Nakano et al. Effect of protonophore on growth of *E. coli*. Journal of Basic Microbiology (1989) vol. 3, pp. 163–169.*

Ghoul et al. Effect of carbonyl cyanide m–chlorophenylhydrazone on *E. coli* halotolerance, Applied and Enviornmental Microbiology, 1989, pp. 1040–1043.*

Bentley and Klebba, "Effect of Lipopolysaccharide Structure on Reactivity of Antiporin Monoclonal Antibodies with the Bacterial Cell Surface," *Journal of Bacteriology* 170(3):1063–1068, 1988.

Kastowsky et al., "Molecular Modelling of the Three–Dimensional Structure and Conformational Flexibility of Bacterial Lipopolysaccharide," *Journal of Bacteriology* 174(14):4798–4806, 1992.

Luk et al., "Epitope Mapping for Four Monoclonal Antibodies Recognizing the Hexose Core Domain of Salmonella Lipopolysaccharide," *The Journal of Biological Chemistry* 266(34):23215–2325, 1991.

Mansfield et al., "Variation in Salmonella core lipopolysaccharide as detected by the monoclonal antibody M105," *Letter in Applied Microbiology* 23:104–106, 1996.

Marino et al., "Energy Dependence of Lipopolysaccharide Translocation in *Salmonella typhimurium*," *The Journal of Biological Chemistry* 260(28):14965–14970, 1985.

Marino et al., "Energy Dependence of O–Antigen Synthesis in *Salmonella typhimurium*," *Journal of Bacteriology* 173(10):3128–3133, 1991.

McGrath and Osborn, "Evidence for Energy–Dependent Transposition of Core Lipopolysaccharide Across the Inner Membrane of *Salmonella typhimurium*," *Journal of Bacteriology* 173(10):3134–3137, 1991.

Pollack et al., "Specificity and Cross–Reactivity of Monoclonal Antibodies Reactive with the Core and Lipid A Regions of Bacterial Lipopolysaccharide," *The Journal of Infectious Diseases* 159(2):168–188, 1989.

Raetz, "Biochemistry of Endotoxins," *Annu. Rev. Biochem.* 59:129–170, 1990.

Raetz, *Escherichia coli and Salmonella*, Second Edition, vol. I, ASM Press, Washington, D.C., 1996, pp. 1035–1063.

Tsang et al., "Structural Differences in the Outer Core Region of Lipopolysaccharides Derived from Members of the Genus Salmonella," *Zbl. Bakt.* 276:330–339, 1992.

Tsang et al., "A Murine Monoclonal Antibody Specific for the Outer Core Oligosaccharide of Salmonella Lipopolysaccharide," *Infection and Immunity* 55(1): 211–216, 1987.

Tsang et al., "A Murine Monoclonal Antibody that Recognizes a Genus–Specific Epitope in the Salmonella Lipopolysaccharide Outer Core," *Zbl. Bakt.* 274: 446–455, 1991.

Tsang et al., "Lack of the α–1,2–linked N–acetyl–D–Glucosamine Epitope in the Outer Core Structures of Lipopolysaccharides from Certain O Serogroups and Subspecies of Salmonella Enterica," *Res. Microbiol.* 142: 521–533, 1991.

(List continued on next page.)

*Primary Examiner*—Jeffrey Stucker
*Assistant Examiner*—Ulrike Winkler
(74) *Attorney, Agent, or Firm*—SEED Intellectual Property Law Group PLLC

(57) ABSTRACT

Compositions, formulae, devices and methods for the detection of target microorganisms, such as by visual immunoprecipitate assay, enzyme linked immunoassay, chemiluminescence, immunoblotting, or similar detection technology, wherein detection requires the discrimination among closely related genera, species and strains of antigenically related microorganisms based on immunological reactivity of a highly conserved antigen epitopes with a reagent system comprised of an antibody linked to a detecting reagent. The invention permits a detectable event to occur by exposing inaccessible but highly conserved and specific antigen epitopes to the detecting reagent. Exposure of such antigen epitopes without inactivating microbial metabolism allows for specific detection.

25 Claims, No Drawings

OTHER PUBLICATIONS

Tsang et al., "Screening for Salmonella with a Murine Monoclonal Antibody M105 Detects both Felix O1 Bacteriophage Sensitive and Resistant Salmonella Strains," *Zbl. Bakt. 286*: 23–32, 1997.

Ohyama et al., "Osmotic Adaption of *Escherichia coli* with a Neglible Proton Motive Force in the Presence of Carbonyl Cyanide m–Chlorophenylhydrazone," *Journal of Bacteriology 174*(9): 2922–2928, 1992.

Rodionov and Ishiguro, "Inhibition of Peptidoglycan Hydrolase Activity in Vivo and in Vitro by Energy Uncouplers in *Escherichia coli*," *Microbial Drug Resistance 2*(1): 131–134, 1996.

Peleg et al. Effects of salts ond ionophores on proline transport in moderatly halophilic halotolerant bacterium. Biochemica et Biophysica Acta. vol. 596 (1998) pp. 118–128.*

Rosson et al. Use of poisons in determenination of microbial manganese binding rates in seawater. Applied Enviornmental Microbiology. vol. 47 (1984) pp. 740–745.*

Tsang et al. Characterization of murine monoclonal antibodies against serotype *B salmonellae* and application as serotyping reagents. Journal of Clinical Microbiology. vol. 29, No. 9 (1991) pp. 1899–1903.*

Bollag et al. Protein Methods, Wiley–Liss Inc., New York (1996) pp. 42–49.*

* cited by examiner

COMPOSITION, FORMULAE, DEVICES AND METHODS FOR CONTROL OF SPECIFICITY AND INCLUSIVITY OF MICROORGANISMS CONTAINING CLOSELY RELATED ANTIGEN EPITOPES

CROSS-REFERENCE TO RELATED APPLICATION

This application is claims priority from U.S. Provisional Application Ser. No. 60/096,566, filed Aug. 14, 1998.

TECHNICAL FIELD

The present invention relates generally to compositions, formulae, devices, and methods for detecting and identifying microorganisms and, more particularly, to compositions, formulae, devices, and methods for detecting microorganisms by exposing highly conserved antigenic sites of target microorganisms without inactivating the microorganisms' ability to grow to sufficient levels to be detected by an antibody linked detection system.

BACKGROUND OF THE INVENTION

Microbial diseases have long been a major health concern worldwide. Significant increase in the frequency and severity of outbreaks have occurred throughout the world. New pathogenic bacteria, such as *E. coli* 0157:H7, have been identified. Furthermore, previously recognized pathogenic genera have mutated to form drug resistant highly infectious strains such as *Salmonella typhimirium* DT 104. A key feature in the prevention of such diseases is early diagnosis. Epidemiologists must look for microbial contamination in the environment as well as in food products to find the effective disease prevention strategies.

One example is the outbreak in 1992 of Enterohemorrhagic *E. coli* (EHEC) in the Pacific Northwest of the United States due to contaminated ground beef. EHEC is a relatively "newly discovered" pathogen. EHEC was first isolated in 1975, and it was not until 1982 that *E. coli* 0157:H7 was associated with two food related outbreaks of hemorrhagic colitis in the United States. The reported incidence of *E. coli 0157*:H7 cases is increasing. Typically, *E. coli* strains are harmless commensals, but a few strains are pathogenic. EHEC is particularly virulent and can trigger deadly complications, including severe abdominal cramps and acute renal failure in children as well as cardiovascular and central nervous system problems.

As another example, Salmonella is the leading cause (more than 50%) of total bacterial foodborne disease outbreaks, according to the United States Centers for Disease Control (CDC) surveillance of foodborne diseases. More than 40,000 cases per year were reported to the CDC during the period 1988–1992. Salmonella can infect a broad variety of warm- and cold blooded animals, and can survive for long periods of time outside a host.

In a further example, *Salmonella typhimurium* DT 104 was first identified in the United Kingdom in the early 1990s. It is a highly adapted drug resistant strain of Salmonella known for its virulence. Resultingly, significant clinical interest has surrounded this serotype. *S. typhimurium* DT 104 contains core cell wall antigen epitopes that are highly conserved among the genus Salmonella.

Listeria, a genus of gram positive bacteria, is widely distributed in nature, having been isolated from soil, water, vegetation and many animal species. The detection frequency for Listeria in the agricultural environment appears to be increasing. For specific outbreaks of listeriosis, estimates place mortality at 30% to 40% of affected patients, however, little is known of the minimum infective dose. One particularly troublesome aspect of Listeria control in foods is that Listeria can grow at temperatures as low as –0.4° C. and as high as 44° C. These factors all contribute to the increasing significance of Listeria as a food pathogen.

*Campylobacter jejuni* and coli have recently been identified as the lead causes of enteritis, especially from poultry sources. This has led to an increased need to discriminate these two species from several other Campylobacter species which are not human pathogens. This requires the differential selection of more specific cell wall membrane antigen epitopes.

The ability to monitor potential environmental and food sources of microbial contamination quickly and easily, but with very high specificity, would reduce the risk of human infection. Therefore, an analytical method which affords high specificity, preferably combined with a device able to assay for microorganisms, including bacteria, yeasts, molds, fungi, parasites and viruses, that requires no special or technical equipment, can be performed in the field and does not require special skills would be useful. In the case of foodborne bacterial contamination, four of the major disease-related organisms are Salmonella, Listeria, EHEC and Campylobacter.

While there are a number of Salmonella, Listeria, and EHEC detection methods presently available, trained laboratory technicians and a minimum of 2–5 days are required to obtain test results by the standard cultural methods of analysis. New, more rapid methods are based on such techniques as enzyme linked immunoassay EIA), DNA hybridization, immunodiffusion, or growth/metabolism measurements. While taking much less time than the cultural methods, these rapid tests still require skilled technical training, a functional laboratory, and specialized equipment. These tests generally take a total of two or more days, including considerable hands-on time. Campylobacter detection methodology to date is technically intensive requiring fastidious media and environmental conditions, in addition to well-trained analysts.

Another recent technology in the diagnostic field involves lateral flow immunoassays. Such tests have been developed for the detection of human chorionic gonadotropin (hCG), and applied to pregnancy testing. Typically, a monoclonal or polyclonal antibody is immobilized in a discrete band near the distal end of a solid carrier strip, called the detection zone. Another amount of antibody is labeled with a detection reagent such as an inorganic sol or dyed polystyrene particle. This labeled antibody is reversibly fixed near the proximal end of the carrier strip. Upon hydration of the proximal end with a sample fluid potentially containing the antigen, the antigen reacts with the labeled antibody and the complex passes through the zone of immobilized antibody, forming a sandwich upon reacting with the immobilized antibody. The capture of the chromogenic reagent-antigen complex causes the formation of a visible signal in the detection zone.

Two major challenges must be addressed to distinguish pathogenic bacteria, as opposed to distinguishing hormones or other soluble molecular targets. These challenges are the need to detect all of the strains of a pathogenic microorganism in the presence of numerous antigenically related organisms, with a low tolerance for false positive results and a very low, preferably zero, tolerance for false negatives. The second challenge is the physical size and heterogeneity of the microorganism itself. A typical clinical diagnostic test, such as a test for hCG in urine, is focused on detecting a single, small, unique entity (ie., a hormone) in a well characterized matrix (e.g., urine). Furthermore, the structure of the analyte (hCG) is defined and uniform in size and composition.

Pathogen detection, for example, a test for Salmonella, must distinguish a particular pathogenic strain from non-pathogenic strains of similar microorganisms, such as Citrobacter spp. and Enterobacter spp. In contrast to the well-defined small size and structure of most hormones or marker proteins, microorganisms are very large, their surfaces are heterogeneous containing many distinct antigen epitopes that can undergo changes, such as the phase-switching of Salmonella flagella.

In addition, the cell wall membrane of many microorganisms contain antigen epitopes, such as lipopolysaccharides, which are repeated with a high degree of consistency within a given genus. These antigen epitopes serve as highly desirable targets for reaction with complimentary specific antibodies which, in turn, provides a method of high accuracy with low false positives. The ability to isolate and bind to antibodies reacting with these highly conserved antigen epitopes is difficult, however, because they can be sterically hindered by O-antigen polysaccharide chains. They are generally inaccessible because of a phenomenon known as steric interference. This steric interference is provided by the surface antigen epitopes of the microorganism. Examples of surface structures known to contribute to this interference are surface proteins, group specific lypopolysaccharides, flagella, and cellular encapsulation.

Although, aggressive treatments are available which will expose interior antigen epitopes, these treatments destroy cell viability and in many cases disrupt cellular integrity completely. Examples of such treatments are heat treatment (boiling or autoclaving) and chemical extraction (nitrous acid digestion). The significant shortcoming of these extractions is that they result in death of the microorganism. Therefore, if the cell population had not reached a sufficiently detectable level prior to inactivation, a negative determination will result.

Thus, there is a need in the art for methodologies that will allow the simultaneous exposure of highly conserved masked antigen epitopes while still allowing the microorganisms to multiply. Further, there is a need in the art to incorporate improved selectivity for highly conserved target antigen epitopes of specific species in a population of heterogeneous microorganisms in a variety of matrices. The present invention provides these and other, related advantages.

SUMMARY OF THE INVENTION

The present invention generally provides a novel, antigenic epitope exposing microorganism growth composition. In one aspect, the invention provides a composition comprising a general enrichment media and at least one structure modifying organic chemical. In one embodiment, the structure modifying organic chemical is 2,4-dinitrophenol or carbonyl cyanide-m-chlorophenyl hydrazone. In another embodiment, the structure modifying organic chemical is 2,4-dinitrophenol. In yet another embodiment, the general enrichment media is selected from a variety of readily made or commercially available media including Terrific Broth, SOB medium, SOC medium, LB medium, NZCYM medium, minimal medium, lactose broth, buffered peptone water, Brain Heart Infusion medium, Haemophilus broth, tryptic soy broth, and nutrient broth.

It is another aspect of the present invention to provide a method for detecting a microorganism in a test sample by contacting the test sample with a composition comprising general enrichment media and at least one structure modifying organic chemical, thereby forming a mixture. This mixture is then incubated for a time sufficient to allow for detectable levels of microorganisms to develop, after which the presence of specific microorganisms is detected. In one embodiment of this aspect of the invention the mixture is contacted with a detergent prior to or contemporaneous with detection. In another embodiment, the mixture is contacted with a detergent and heated prior to or contemporaneous with detection. In one embodiment, the detergent is anionic. In yet another embodiment, the detergent is non-ionic. In certain embodiments, the anionic detergent may be selected from sodium dodecyl sulfate and sodium deoxycholate. In certain embodiments, the non-ionic detergent is NP-40, tergitol, or triton X-100. In certain other embodiments, the mixture is heated in the presence of the detergent to a temperature, between 40° C. and 121° C.

In certain embodiments of the detection method, the microorganism detected is Listeria, Enterohemorrhagic *E. coli*, Salmonella, or Campylobacter.

Turning to another aspect of the invention, a method is provided for detecting the presence of Listeria, Enterohemorrhagic *E. coli*, Salmonella, or Campylobacter in a test sample wherein the test sample is contacted with a composition comprising general enrichment media and at least one structure modifying organic chemical, followed by incubation of this mixture for a time sufficient to allow for detectable levels of microorganisms to develop. Subsequent to the development of detectable levels of microorganisms in the mixture, the presence of Listeria, Enterohemorrhagic *E. coli*, Salmonella, or Campylobacter is specifically detected. In one embodiment of this aspect of the invention the mixture is contacted with a detergent prior to or contemporaneous with detection. In another embodiment, the mixture is contacted with a detergent and heated prior to or contemporaneous with detection. In one embodiment, the detergent is anionic. In yet another embodiment, the detergent is non-ionic. In certain embodiments, the anionic detergent may be sodium dodecyl sulfate or sodium deoxycholate. In certain embodiments, the non-ionic detergent is NP-40, tergitol, or triton X-100. In certain other embodiments, the mixture is heated in the presence of the detergent to a temperature, between 40° C. and 121° C.

In another embodiment, the detection methodologies described herein utilize an immunoassay. In certain embodiments, the immunoassay is selected from a visual immunoprecipitate assay, an enzyme linked immunoassay, chemiluminescence, and immunoblotting. In certain other embodiments, the immunoassay is a visual immunoprecipitate assay. Also provided in certain embodiments are immunoassays which utilize a complementary monoclonal antibody, polyclonal antibody, or an antibody fragment, wherein said antibody or antibody fragment is specific for a highly conserved cell wall epitope in the target microorganism.

In another aspect of the invention, a method is provided, comprising contacting a test sample containing a microorganism with an immunoaffinity based detection device, wherein the test sample has been previously propagated in the presence of a structure modifying organic chemical.

The invention also provides a method for propagating a microorganism such that cell wall antigen epitopes of the microorganism are altered by contacting a test sample with a composition comprising general enrichment media and at least one structure modifying organic chemical, and propagating the microorganism therein.

Turning to yet another aspect of the invention, a method for detecting microorganism specific epitopes on a target microorganism in a test sample is provided, comprising propagating a microorganism in a test sample in a permissive general enrichment media, wherein said media comprises a structure modifying organic chemical, and contacting the test sample with a microorganism specific antibody linked to a detecting reagent, wherein reaction with the antibody indicates the presence of the microorganism. In further embodiment, contact between the test sample and the antibody occurs in device or assay system. In yet another embodiment, the assay system is selected from a visual immunoprecipitate assay, an enzyme linked immunoassay, chemiluminescence, and immunoblotting. In another embodiment, the assay device is a lateral flow detection device. In certain embodiments, the antibody used in the above methods is specific for a microorganism selected from Salmonella, Enterohemorrhagic E. coli, Listeria, and Campylobacter.

It is another aspect of the present invention to provide a lateral flow device for detecting a target microorganism in a sample comprising a microorganism specific antibody and a test sample previously propagated in a general enrichment media, the media comprising at least one structure modifying organic chemical. In another embodiment of this aspect of the invention the antibody is specific for any one of Salmonella, Enterohemorrhagic E. coli, Listeria, or Campylobacter.

These and other aspects of the present invention will become evident upon reference to the following detailed description and examples. In addition, the various references set forth below describe in more detail certain procedures or compositions (e.g., antibodies, detection methodologies, etc.), and are therefore each incorporated herein, by reference, in their entirety.

DETAILED DESCRIPTION OF THE INVENTION

Prior to setting forth the invention, it may be helpful to an understanding thereof to set forth definitions of certain terms that will be used hereinafter.

The term "antibody" as used herein includes polyclonal, monoclonal, humanized, chimeric, and anti-idiotypic antibodies, as well as fragments thereof such as F(ab')$_2$ and Fab fragments and other recombinantly produced binding partners. Further, the antibodies may be covalently linked to or recombinantly fused to an enzyme, such as alkaline phosphatase, horse radish peroxidase, α-galactosidase, and the like.

"Structure modifying organic chemical" refers to an organic chemical capable of altering the composition of the cell wall of a microorganism, such that specific and conserved ligands are exposed. Briefly, such organic chemicals typically inhibit the transfer of sterically interfering epitopes to the cell wall. Such organic chemicals include, but are not limited to, 2,4-dinitrophenol, carbonyl cyanide-m-chlorophenyl hydrazone or similar electron uncouplers (i.e., disabling proton motive force), which have the effect of exposing high affinity and specific epitopes which are recognized by monoclonal or polyclonal antibodies.

The term "general enrichment media" refers to any media which is known to be useful for facilitating the growth of microorganisms. Briefly, a variety of general enrichment media are commercially available and/or can be readily made, these include, but are not limited to, Tryptone based medium (e.g., Terrific Broth, SOB, SOC, and LB medium), NZCYM medium, minimal medium, lactose broth, buffered peptone water, Brain Heart Infusion medium, Haemophilus broth, Tryptic Soy broth, Nutrient broth and the like (see Sambrook et al., *Molecular Cloning: A Laboratory Manual*, $2^{nd}$ ed., Cold Spring Harbor Press, 1989; Ausubel et al., *Current Protocols in Molecular Biology*, Greene Publishing, 1995; commercially available from Sigma Chemical Co, St. Louis, Mo. and Difco Laboratories Inc., Detroit, Mich.).

The present invention provides for the detection of target microorganisms which express highly conserved but sterically inaccesible antigen epitopes by combining an inventive composition of growth media followed by detection with very specific antibodies using a detection format, such as a visual immunoprecipitation assay, enzyme linked immunoassay, chemiluminescence, immunoblotting, or similar technology. The present invention permits such detection by providing a growth environment in a modified culture medium wherein the microorganisms are permitted to multiply to optimal levels but their surface structure is altered, without causing substantial cell death, to expose the highly specific and conserved antigen epitopes found in the interior cell wall structure.

Using the present invention the analyst can incubate the test sample of interest under routine laboratory conditions in the presence of the inventive growth medium which exposes the specific antigen epitopes. This invention provides a highly accurate test result while still affording the analyst with the convenience of standard microbiological laboratory conditions. A further aspect of the present invention is that no unique or costly equipment and facilities are required.

Since continued cell viability is important to allow the pathogen of interest to grow to sufficient numbers for detection by the chosen detection system (e.g., visual immunoprecipitate assay, enzyme linked immunoassay, chemiluminescence, immunoblotting, or similar immunoaffinity based detection technology), the present invention utilizes methodologies which simultaneously induce altered cell wall compositions as well as allowing for further growth of the pathogen. More specifically, the present invention is directed to a highly specific detection of target microorganisms by contacting samples potentially containing these microorganisms in the presence of a growth medium containing structure modifying organic chemicals which allow the expression and accessibility of these highly conserved antigen epitopes to specific monoclonal or polyclonal detecting antibodies bound to detecting reagents. Detection is accomplished by means a visual immunoprecipitate assay, enzyme linked immunoassay, chemiluminescence, immunoblotting, or similar immuno-affinity based detection technology. The present invention permits such detection by modifying the surface structure of the target microorganism without causing substantial cell death in such a manner that the more highly conserved and specific antigen epitopes are made accessible to the corresponding antibodies linked to detecting reagents.

The media composition of the present invention biochemically modifies the metabolism of the target microorganism so that it produces a modified cell wall which exposes the most specific and conserved epitopes. (See, e.g., Tsang et al., "Screening for Salmonella with a Murine Monoclonal Antibody M105 Detects both Felix O1 Bacteriophage Sensitive and Resistant Salmonella Strains," *Zbl. Bakt.* 286:23–32, 1997; Tsang et al., "A Murine Monoclonal Antibody that Recognizes a Genus-Specific Epitope in the Salmonella Lipopolysaccharide Outer Core," *Zbl.Bakt.* 274: 446–455, 1991; Tsang et al., "A Murine Monoclonal Antibody Specific for the Outer Core Oligosaccharide of Salmonella Lipopolysaccharide," *Infection and Immunity*, 55: 211–216, 1987; Tsang et al., "Lack of the α-1,2-linked N-acetyl-D-glucosamine epitope in the outer core structures of lipopolysaccharides from the certain O serogroups and subspecies of *Salmonella enterica*," *Res. Microbiol.* 142: 521–533, 1991). The structural modification occurs without inhibiting the microorganisms ability to grow, therefore, the target pathogen microorganism continues to grow uninhibited to reach a detectable level. The combination of structural modification and the ability to further replicate provides an advantage in that the pathogenic microorganisms are generally found in a sample at levels below the detection threshold of most rapid detection systems. While any detection system may be employed, preferred detection systems include, but are not limited to, visual immunoprecipitate assay, enzyme linked immunoassay, chemiluminescence, immunoblotting, and similar detection systems.

In one embodiment of the present invention, a test sample potentially containing a pathogenic microorganism is contacted with a growth medium containing an inhibitor of O-antigen polysaccharide cell surface expression. Subsequently, the sample containing media is subjected to a detection methodology, which may include visual immunoprecipitate assay, enzyme linked immunoassay, chemiluminescence, immunoblotting, or similar detection systems.

In preferred embodiments, the compositions, formulae, detection devices, and the methods of detecting are specific for Listeria, Enterohemorrhagic *E. coli* (EHEC), Salmonella, or Campylobacter. In a particularly preferred embodiment, the inventive growth medium, following incubation, is introduced into a detection system, such as a visual immunoprecipitate assay, an enzyme linked immunoassay, chemiluminescence, immunoblotting, or similar detection technology containing an antibody specific for the target microorganism thereby producing a highly accurate result.

The present invention combines any of several widely recognized general enrichment media such as tryptic soy broth, nutrient broth, buffered peptone water, lactose broth, brain heart infusion broth, or similar media with a number of antigen structure modifying organic chemicals, including but not limited to 2,4-dinitrophenol, carbonyl cyanide-m-chlorophenyl hydrazone or similar electron uncouplers to expose epitopes which are recognized by monoclonal or polyclonal antibodies which have high affinity for the specific epitopes. The mechanism of action of these organic chemicals is to alter the metabolic pathways of the target microorganism such that it produces a deficient cell wall allowing exposure of the interior specific epitopes. It is the combination of the alteration of a metabolic pathway which alters the structure of the cell wall with an antibody-detection reagent contained in a detection device such as visual immunoprecipitate assay which makes the detection rapid and specific.

Following incubation in the inventive media under permissive conditions the results are detected preferably using a rapid detection method such as, but not limited to, visual immunoprecipitate assay, enzyme linked immunoassay, chemiluminescence, immunoblotting, or similar detection technology. Such methodologies are described in greater detail in U.S. Pat. No. 5,658,747 and PCT WO 95/30903. In a preferred embodiment of the invention, the mixture of the composition and the test sample, following incubation, may be exposed to a detergent solution to improve the accessibility of the conserved antigen epitope. In a most preferred embodiment of the invention the detergent may be heated to facilitate a more rapid exposure of the epitope. In yet another embodiment, the mixture, following incubation, is exposed to detergent at an elevated temperature, the temperature is preferably from about 40° C. to 121° C. for a specified time, preferably from two minutes to one hour.

In one embodiment, the mixture, prior to detection, compromises up to about 0.02–2.0% by a weight of a detergent, preferably an anionic detergent, further preferably selected the group consisting of sodium dodecyl sulfate (SDS) and sodium deoxycholate, and the like, but also including non-ionic detergents such as NP-40, tergitol and Triton X-100, and the like.

An additional aspect of the present invention is the use of a visual immunoprecipitate assay to detect the presence of a microorganism in a test sample. In the visual immunoprecipitate assay, the antibodies, including the "antibody-detection-reagent" initially located in the reagent zone, is typically either a polyclonal or monoclonal antibody. Further, when using a polyclonal antibody the antibody is preferably affinity column purified prior to its utilization the present invention. The production of such antibodies is well known in the art. (See, e.g., *Antibodies: A Laboratory Manual*, Harlow and Lane (eds.), Cold Spring Harbor Laboratory Press, 1988). Suitable affinity purified antibodies can also be procured from commercially available sources. For example, a polyclonal antisera specific for Salmonella is available from Kirkegaard and Perry Laboratories, Gaithersburg, Md. A preferred visual immunoprecipitate assay is that which is described by U.S. Pat. No. 5,658,747. Briefly, U.S. Pat. No. 5,658,747 utilizes a lateral flow diagnostic device which comprises a reagent zone containing an antibody-detection reagent and a detection zone located downstream of the reagent zone and comprising an immobile binding partner capable of specifically binding said complex between the target microorganism and the antibody detection reagent.

Polyclonal antibodies can be readily generated by one of ordinary skill in the art via immunization of a variety of warm-blooded animals such as horses, cows, goats, sheep, dogs, chickens, turkeys, rabbits, mice, or rats. Briefly, the target microorganism, or an antigen specifically associated with the target microorganism, is utilized to immunize the animal. The immunogenicity of the protein or peptide of interest may be increased through the use of an adjuvant such as Freund's complete or incomplete adjuvant or by coupling to another protein such as ovalbumin or keyhole limpet hemocyanin (KLH).

Monoclonal antibodies can also be readily generated using well-known techniques. (See, e.g., *Monoclonal Antibodies, Hybridomas: A New Dimension in Biological Analyses*, Plenum Press, Kennett, McKearn, and Bechtol (eds.), 1980, and *Antibodies: A Laboratory Manual*, Harlow and Lane (eds.), supra.) Briefly, as one example, a subject animal is immunized as with the production of a polyclonal antibody. Alternatively, in vitro immunization techniques suitable for the production of monoclonal antibodies are also known in the art. Antibody-producing cells are then fused to immortal myeloma cells to provide an immortal hybridoma cell line. Following the fusion, the cells are placed into culture plates containing a suitable medium, traditionally HAT medium, although other suitable media are known in the art. After about seven days, the resulting fused cells or hybridomas may be screened in order to determine the presence of antibodies which recognize the desired antigen.

Following several clonal dilutions and reassays, hybridoma producing antibodies that bind to the protein of interest can be isolated.

Other techniques can also be utilized to construct monoclonal antibodies or binding partners. (See, e.g., Huse et al., "Generation of a Large Combinational Library of the Immunoglobulin Repertoire in Phage Lambda," *Science* 246:1275–1281, 1989; Sastry et al., "Cloning of the Immunological Repertoire in *Escherichia coli* for Generation of Monoclonal Catalytic Antibodies: Construction of a Heavy Chain Variable Region-Specific cDNA Library," *Proc. Natl. Acad. Sci. USA* 86:5728–5732, 1989; Alting-Mees et al., "Monoclonal Antibody Expression Libraries: A Rapid Alternative to Hybridomas," *Strategies in Molecular Biology* 3:1–9, 1990; Larrick et al., "Polymerase Chain Reaction Using Mixed Primers: Cloning of Human Monoclonal Antibody Variable Region Genes From Single Hybridoma Cells," *BioTechnology* 7:934–938, 1989.)

Once a suitable antibody has been obtained, it may be isolated or purified by many techniques well known to those of ordinary skill in the art (see *Antibodies: A Laboratory Manual*, Harlow and Lane, supra).

Antibodies useful in the present invention are preferably capable of selectively detecting all of the strains of a target microorganism in the presence of numerous antigenically related organisms. Further, the antibodies are preferably capable of such detection with a low tolerance for non-specific binding (which leads to a false positive result) and a very low, preferably zero, failure to bind target the microorganism (which leads to a false negative result).

One aspect of the present invention provides a general enrichment medium, tryptic soy broth, containing 0.1–5 mM 2,4-dinitrophenol to which a test sample is added, thereby forming a mixture, and subsequently incubated at 37° C. for 6–8 hours. Following incubation, an aliquot of the sample is exposed to 0.05–0.5% SDS at 100° C. for ten minutes. The sample may then introduced into a detection device, for example, a visual immunoprecipitate assay device and observed for the formation of a visual line.

Preferably, the sample is a solution containing, or consisting essentially of, an unpurified field sample such as a food sample, an environmental sample such as water or dirt. Alternatively, the sample may be a biological fluid such as a body fluid. In a further embodiment, the sample may be partially or substantially purified prior to administration to the diagnostic device, such as a laboratory sample. Upon contacting the sample with a composition containing a specific antibody-detection reagent for the target microorganism that is potentially contained within the sample, binding between the antibody-detection reagent and the target microorganism is permitted, thereby detecting the presence or absence of a particular pathogenic microorganism.

Another aspect of the present invention provides a method for detecting a microorganism in a test sample wherein the test sample is incubated in a general enrichment media comprising at least one structure modifying organic chemical for sufficient time to propagate detectable levels of microorganisms. Subsequently, the presence of pathogenic microorganisms is detected by utilizing immuno-based detection methodologies, which include but are not limited to, immuno-affinity, visual immunoprecipitation, enzyme linked immunoassay, chemiluminescence, immunoblotting, and the like. Alternatively, the exposure of antigen in a sample may be enhanced by treatment with detergent prior to or contemporaneously with detection. In a further alternative embodiment, the exposure of antigen in a sample, previously subject to propagation in the presence of the composition of the present invention, may be enhanced by heating the sample in the presence of the detergent, prior to or contemporaneously with detection.

In yet another aspect, the present invention provides methods of detecting a target microorganism comprising contacting a sample potentially containing the target microorganism in the presence of other genera not of interest but expressing cross reactive antigen epitopes with a composition as described above under permissive incubation conditions. Following incubation the sample is exposed to an assay such as the visual immunoprecipitate assay that permits the antibody-detection reagent to bind to the target microorganism to provide a complex between the target microorganism and the antibody-detection reagent. The complex then migrates downstream along the lateral flow membrane to a detection zone containing an immobile antibody capable of binding to the complex to provide a bound complex. Next, the bound complex is detected.

The following examples are presented for the purpose of illustration, not limitation.

EXAMPLES

Example 1

Nine strains of Salmonella were identified which were non-reactive in a visual immunoprecipitate assay. The strains were reported to produce excessive levels of surface antigen. It was hypothesized that growth of the strains in the inventive media would eliminate or significantly reduce the expression of surface O group antigen epitopes, thereby allowing detection by highly specific monoclonal antibodies directed against the core region of lypopolysaccharide contained in the visual immnunoprecipitate assay device.

The organisms were grown in the inventive medium, followed by extraction with 0.1% SDS at 100° C. for ten minutes. Strong reactivity was demonstrated. The inventive media formulation was a commercially available formulation of tryptic soy broth containing the following ingredients supplemented with 0.5 mM (0.01%) 2,4-dinitrophenol.

| Trypticase Soy Broth | |
|---|---|
| Pancreatic Digest of Casein | 17.0 g |
| Papaic Digest of Soybean Meal | 3.0 g |
| Sodium Chloride | 5.0 g |
| Dipotassium Phosphate | 2.5 g |
| Dextrose | 2.5 g |
| Distilled Water | 1000 ml |

Example 2

Two strains of Salmonella, serogroups A and B, were determined to be weakly reactive in a monoclonal antibody based visual immunoprecipitate assay and an enzyme linked immunoassay in the presence of related competitive microorganisms. These strains were incubated in the inventive medium in a 1000 fold excess of competitive bacteria, and found to be highly reactive. The inventive media formulation was a commercially available formulation of buffered peptone water supplemented with 0.5 mM (0.01%) 2,4-dinitrophenol.

| Buffered Peptone | |
| --- | --- |
| Pancreatic Digest of Gelatin | 10.0 g |
| Sodium Chloride | 5.0 g |
| Disodium Phosphate | 3.5 g |
| Monopotassium Phosphate | 1.5 g |
| Distilled Water | 1000 ml |

Example 3

A strain of *E. coli* 0157:H7 was found to be weakly reactive in a polyclonal antibody based assay. The strain was grown in the inventive medium and the sensitivity was improved by 100 fold. The media was a modified tryptic soy broth with 20 mg/ml novobiocin supplemented with 0.5 mM (0.01%) 2,4-dinitrophenol.

| Modified Tryptic Soy Broth | |
|---|---|
| Bacto Tryptone | 17.0 g |
| Bacto Soytone | 3.0 g |
| Sodium Chloride | 5.0 g |
| Dipotassium Phosphate | 4.0 g |
| Bile Salts No. 3 | 1.5 g |
| Bacto Dextrose | 2.5 g |

Example 4

A pathogenic strain of *Campylobacter jejuni* was identified which did not react in a polyclonal/monoclonal based enzyme immunoassay. The strain was grown in the inventive medium followed by treatment with 0.1% sodium dexoycholate and was found to be strongly reactive. The media was Campylobacter isolation broth supplemented with 0.5 mM (0.01 %) 2,4-dinitrophenol.

| Nutrient Broth No. 2 with 0.6% yeast extract | |
|---|---|
| Lab-Lemco Powder | 10.0 g |
| Peptone | 10.0 g |
| Sodium Chloride | 5.0 g |
| Yeast Extract | 6.0 g |
| Distilled Water | 1000 ml |

From the foregoing, it will be appreciated that, although specific embodiments of the invention have been described herein for purposes of illustration, various modifications may be made without deviating from the spirit an scope of the invention. Accordingly, the invention is not to be limited except as by the appended claims.

We claim:

1. A method for detecting a microorganism in a test sample, comprising:

(a) contacting a test sample with a composition comprising general enrichment media and at least one structure modifying organic chemical, thereby forming a mixture;

(b) incubating the mixture for at least 6 hours to allow for detectable levels of microorganisms to develop, and (c) detecting the presence of specific microorganisms in the mixture; and wherein said structure modifying organic chemical is 0.1–5 mm 2,4 dinitrophenol.

2. The method of claim 1, wherein the preferred time sufficient to allow for detection is about 6–8 hours.

3. The method according to claim 1, wherein the microorganism is selected from the group consisting of Listeria, Enterohemorrhagic *E. coli*, Salmonella, and Campylobacter.

4. The method according to claim 1, further comprising contacting the mixture with a detergent, wherein said contact further exposes antigenic epitopes prior to detection, and wherein said detergent is present in an amount of about 0.02% to 2% by weight of detergent.

5. The method according to claim 4, further comprising heating the combination of the mixture and the detergent prior to detection.

6. The method according to either claim 4 or 5, wherein the detergent is an anionic detergent.

7. The method according to claim 5, wherein the detergent is selected from the group consisting of sodium dodecyl sulfate and sodium deoxycholate.

8. The method according to claim 4 or 5, wherein the detergent is a non-ionic detergent.

9. The method according to claim 8, wherein the detergent is selected from the group consisting of NP-40, tergitol, and triton X-100.

10. The method according to claim 5, wherein heating is performed at about 40° C. to about 121° C. for two minutes to one hour to further expose antigenic epitopes.

11. A method for detecting the presence of Listeria, Enterohemorrhagic *E. coli*, Salmonella, or Campylobacter in a test sample, comprising:

(a) contacting a test sample with a composition comprising general enrichment media and at least one structure modifying organic chemical, thereby forming a mixture;

(b) incubating the mixture for at least 6 hours to allow for detectable levels of microorganisms to develop;

(c) detecting the presence of specific microorganisms in the mixture, wherein a positive detection result indicates the presence of Listeria, Enterohemorrhagic *E. coli*, Salmonella, or Campylobacter in the test sample; and wherein said structure modifying organic chemical is 0.1–5 mm 2,4-dinitrophenol.

12. The method according to claim 11, further comprising contacting the mixture with a detergent, wherein said contact further exposes antigenic epitopes prior to detection, and wherein said detergent is present in an amount of about 0.02% to 2% by weight of detergent.

13. The method according to claim 12, further comprising heating the combination of the mixture and the detergent prior to detection.

14. The method according to claim 12 or 13, wherein the detergent is an anionic detergent.

15. The method according to claim 13, wherein the detergent is selected from the group consisting of sodium dodecyl sulfate and sodium deoxycholate.

16. The method according to claim 12 or 13, wherein the detergent is a non-ionic detergent.

17. The method according to claim 16, wherein the detergent is selected from the group consisting of NP-40, tergitol, and triton X-100.

18. The method according to claim 12, wherein heating is performed at about 40° C. to about 121 ° C. for two minutes to one hour to further expose antigenic epitopes.

19. The method according to claim 11, wherein detection occurs by an immunoassay.

20. The method according to claim 19, wherein the immunoassay is selected from the group consisting of a visual immunoprecipitate assay, an enzyme linked immunoassay, chemiluminescence, and immunoblotting.

21. The method according to claim 20, wherein the immunoassy is a visual immunoprecipitate assay.

22. The method according to claim 20, wherein the detection utilizes a complementary monoclonal antibody, polyclonal antibody, or an antibody fragment, and wherein said antibody or antibody fragment is specific for a highly conserved cell wall epitope.

23. A method for detecting a microorganism in a test sample, comprising contacting a test sample containing a microorganism with an immunoaffinity based detection device, wherein said test sample has been previously propagated in the presence of a structure modifying organic chemical; and wherein said structure modifying organic chemical is 0.1–5 mm 2,4-dinitrophenol.

24. A method for detecting microorganism specific epitopes on a target microorganism in a test sample, comprising:

(a) propagating a microorganism in a test sample in a permissive general enrichment media, wherein said media comprises a structure modifying organic chemical;

(b) contacting the test sample with a microorganism specific antibody linked to a detecting reagent, wherein reaction with the antibody indicates the presence of the microorganism; and wherein said structure modifying organic chemical is 0.1–5 mm 2,4-dinitrophenol.

25. The method of any one of claims 1, 11, 23, and 24, wherein said test sample is selected from the group consisting of a food product, water, an environmental sample, a biological sample, a human specimen, and a veterinary sample.

* * * * *

UNITED STATES PATENT AND TRADEMARK OFFICE
CERTIFICATE OF CORRECTION

PATENT NO.    : 6,379,918 B1
DATED         : April 30, 2002
INVENTOR(S)   : Philip T. Feldsine et al.

It is certified that error appears in the above-identified patent and that said Letters Patent is hereby corrected as shown below:

Column 11,
Line 67, "0.1-5 mm 2,4 dinitrophenol" should be corrected to read -- 0.1-5 mM 2,4 dinitrophenol --.

Column 12,
Line 40, "0.1-5 mm 2,4 dinitrophenol" should be corrected to read -- 0.1-5 mM 2,4 dinitrophenol --.
Line 59, "The method according to claim 12," should be corrected to read -- The method according to claim 13, --.

Column 13,
Line 14, "0.1-5 mm 2,4 dinitrophenol" should be corrected to read -- 0.1-5 mM 2,4 dinitrophenol --.

Column 14,
Line 9, "0.1-5 mm 2,4 dinitrophenol" should be corrected to read -- 0.1-5 mM 2,4 dinitrophenol --.

Signed and Sealed this

Eighth Day of October, 2002

*Attest:*

JAMES E. ROGAN
*Attesting Officer*      *Director of the United States Patent and Trademark Office*